US012727947B2

(12) United States Patent
True et al.

(10) Patent No.: US 12,727,947 B2
(45) Date of Patent: Sep. 8, 2026

(54) SYSTEMS AND METHODS UTILIZING MACHINE-LEARNING FOR IN VIVO NAVIGATION

(71) Applicant: Boston Scientific Scimed, Inc., Maple Grove, MN (US)

(72) Inventors: Kyle True, Minneapolis, MN (US); Daniel J. Foster, Lino Lakes, MN (US); Sebastian Ordas Carboni, Vadnais Heights, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 732 days.

(21) Appl. No.: 17/807,893

(22) Filed: Jun. 21, 2022

(65) Prior Publication Data

US 2022/0401154 A1 Dec. 22, 2022

Related U.S. Application Data

(60) Provisional application No. 63/213,458, filed on Jun. 22, 2021.

(51) Int. Cl.
*A61B 34/20* (2016.01)
*A61B 90/00* (2016.01)
*G06T 7/70* (2017.01)

(52) U.S. Cl.
CPC ................ *A61B 34/20* (2016.02); *G06T 7/70* (2017.01); *A61B 2034/2063* (2016.02); (Continued)

(58) Field of Classification Search
CPC ............................................. A61B 2034/2063
See application file for complete search history.

(56) References Cited

U.S. PATENT DOCUMENTS 10,098,565 B2 10/2018 Brannan et al.
2011/0237934 A1* 9/2011 Onishi .................... A61B 8/12 600/424

(Continued)

FOREIGN PATENT DOCUMENTS

JP 2015107268 A 6/2015
JP 2015530903 A 10/2015

(Continued)

OTHER PUBLICATIONS

International Search Report and Written Opinion issued in International Application No. PCT/US2022/073050, issued Oct. 20, 2022 (13 pages).

*Primary Examiner* — Wen W Huang
(74) *Attorney, Agent, or Firm* — Bookoff McAndrews, PLLC

(57) ABSTRACT

A method of providing in vivo navigation of a medical device includes: receiving input medical imaging data of a patient's anatomy; receiving input non-optical in vivo image data from a sensor on a distal end of the device in the anatomy; using a trained model to locate the distal end in the input imaging data, wherein: the model is trained, based on (i) training medical imaging data and training non-optical in vivo image data of one or more individuals' anatomy and (ii) registration data associating the training image data with locations in the training imaging data as ground truth, to learn associations between the training image data and the training imaging data; determining an output location of the medical device using the learned associations and the input data; modifying the input imaging data to depict the determined location; and causing a display to output the modified input imaging data.

20 Claims, 8 Drawing Sheets

(52) U.S. Cl.
CPC . *A61B 2034/2065* (2016.02); *A61B 2090/364* (2016.02); *A61B 2090/378* (2016.02); *G06T 2207/10132* (2013.01); *G06T 2207/20081* (2013.01); *G06T 2207/30061* (2013.01)

(56) References Cited

U.S. PATENT DOCUMENTS

| | | | | |
|---|---|---|---|---|
| 2013/0245433 | A1* | 9/2013 | Deladi | A61B 8/445<br>600/424 |
| 2013/0281821 | A1 | 10/2013 | Liu et al. | |
| 2018/0140359 | A1* | 5/2018 | Koyrakh | A61B 34/20 |
| 2018/0279852 | A1* | 10/2018 | Rafii-Tari | G16H 40/63 |
| 2019/0046071 | A1 | 2/2019 | Brannan et al. | |
| 2019/0142528 | A1 | 5/2019 | Vertikov | |
| 2019/0355149 | A1* | 11/2019 | Avendi | A61B 34/20 |
| 2020/0121376 | A1* | 4/2020 | Zhang | A61B 18/1815 |
| 2020/0179062 | A1 | 6/2020 | Hunter et al. | |
| 2020/0297444 | A1 | 9/2020 | Camarillo et al. | |
| 2020/0397511 | A1* | 12/2020 | Ishrak | A61F 2/2427 |
| 2020/0405399 | A1 | 12/2020 | Steinberg et al. | |
| 2021/0282857 | A1* | 9/2021 | Bell | A61B 17/1626 |
| 2022/0142713 | A1* | 5/2022 | Oren | A61B 5/287 |
| 2023/0008714 | A1* | 1/2023 | Rajguru | A61B 5/1076 |
| 2023/0233196 | A1* | 7/2023 | Ito | A61B 10/06<br>600/562 |

FOREIGN PATENT DOCUMENTS

| | | | |
|---|---|---|---|
| JP | 2018532467 | A | 11/2018 |
| WO | WO 2020/148450 | | 7/2020 |

* cited by examiner

SYSTEMS AND METHODS UTILIZING MACHINE-LEARNING FOR IN VIVO NAVIGATION

CROSS-REFERENCE TO RELATED APPLICATIONS

This application claims the benefit of priority of U.S. Provisional Patent Application No. 63/213,458, filed Jun. 22, 2021, the entirety of which is incorporated herein by reference.

TECHNICAL FIELD

Various embodiments of this disclosure relate generally to machine-learning-based techniques for in vivo navigation, and, more particularly, to systems and methods for determining registration between non-optical image data, e.g., ultrasound imaging data, and medical imaging data.

BACKGROUND

In certain medical procedures, a medical device is advanced, at least in part, into the body of a patient. For example, during a lung ablation procedure to remove undesirable tissue from within the lung of a patient, an ablation device is advanced into the peripheral portion of the lung having the undesirable tissue. While techniques using direct insertion, e.g., via a needle, have been used, such techniques generally have a high risk of complications. Less invasive techniques have been developed, such as techniques utilizing a bronchoscope. However, such techniques may also have disadvantages.

This disclosure is directed to addressing above-referenced challenges. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY OF THE DISCLOSURE

According to certain aspects of the disclosure, methods and systems are disclosed for providing in vivo navigation of a medical device.

In one aspect, an exemplary embodiment of a system for providing in vivo navigation of a medical device may include a memory, a display, and a processor operatively connected to the display and the memory. The memory may store instructions and a trained machine-learning model. The machine-learning model may have been trained, based on (i) training medical imaging data and training non-optical in vivo image data of at least a portion of an anatomy of one or more individuals and (ii) registration data associating the training non-optical in vivo image data with locations in the training medical imaging data as ground truth. The training may have been configured to cause the trained machine-learning model to learn associations between the training non-optical in vivo image data and the training medical imaging data. The processor may be configured to execute the instructions in the memory to perform operations. The operations may include: receiving input medical imaging data associated with at least a portion of an anatomy of a patient; receiving input non-optical in vivo image data from a sensor positioned on a distal end of a medical device that is advanced into the portion of the anatomy of the patient; using the learned associations to determine a location of the distal end of the medical device in the input medical imaging data; modifying the input medical imaging data to include a location indicator indicative of the determined location of the distal end of the medical device; and causing the display to output the modified input medical imaging data including the location indicator.

In some embodiments, the operations may further include: upon the medical device moving within the portion of the anatomy of the patient, receiving further non-optical in vivo image data from the sensor; using the learned associations to determine an updated location of the distal end of the medical device based on the further non-optical in vivo image data; updating the input medical imaging data to adjust the location indicator based on the updated location of the distal end of the medical device; and causing the display to output the updated input medical imaging data.

In some embodiments, determining of the updated location, the updating of the input medical imaging data, and the output via the display of the updated input medical imaging data may occur in real-time or near real-time such that the display is configured to output a live location of the distal end of the medical device.

In some embodiments, the trained machine-learning model may be configured to learn associations between a sequence of non-optical in vivo images of the training non-optical in vivo image data and a path of travel within the training medical imaging data.

In some embodiments, the trained machine learning-model may be configured to determine the location of the distal end of the medical device in the input medical imaging data by predicting a path of travel of the distal end of the medical device from a previous location in the input medical imaging data using the input non-optical in vivo image data.

In some embodiments, the operations may further include: extracting at least one three-dimensional structure from the input non-optical in vivo image data; and registering the at least one three-dimensional structure with geometry of the at least portion of the anatomy from the input medical imaging data. In some embodiments, the determination of the location of the distal end of the medical device may be further based on the registration of the at least one three-dimensional structure with the geometry.

In some embodiments, the trained machine-learning model may include one or more of a long short term memory network or a sequence-to-sequence model.

In some embodiments, the operations may further include receiving a position signal from a position sensor positioned proximate to the distal end of the medical device. In some embodiments, the determination of the location of the distal end of the medical device may be further based on the position signal.

In some embodiments, the operations may further include using the position signal to localize a position of the distal end of the medical device to a region within the portion of the anatomy of the patient. In some embodiments, using the learned associations to determine the location of the distal end of the medical device in the input medical imaging data may include using the learned associations to identify the location of the distal end within the localized region.

In some embodiments, the input non-optical in vivo image data may include 360 degree image data from a phased transducer array.

In some embodiments, the training may be configured to associate the training non-optical in vivo image data with diameters of interior portions of anatomy. In some embodiments, determining the location of the distal end of the medical device using the learned associations may include: using the learned associations to determine a diameter of an interior portion of the anatomy of the patient at a current location of the distal end of the medical device; and comparing the current diameter with geometry of the input medical imaging data to identify a location in the input medical imaging data matching the determined diameter.

In some embodiments, the trained machine-learning model may be configured to learn associations between a sequence of diameters determined based on the training non-optical in vivo image data and a path of travel within the training medical imaging data. In some embodiments, the trained machine learning-model may be configured to determine the location of the distal end of the medical device in the input medical imaging data by predicting a path of travel of the distal end of the medical device from a previous location in the input medical imaging data using the input non-optical in vivo image data.

In some embodiments, the portion of the anatomy of the patient may include a peripheral portion of a lung of the patient.

In some embodiments, the input non-optical in vivo image data may include ultrasound data.

In some embodiments, the trained machine learning-model may be configured to determine the location of the distal end of the medical device in the input medical imaging data based on shape information associated with the medical device received from a further sensor of the medical device.

In another aspect, an exemplary embodiment of a method for providing in vivo navigation of a medical device may include: receiving input medical imaging data associated with at least a portion of an anatomy of a patient; receiving input non-optical in vivo image data from a sensor positioned on a distal end of a medical device that is advanced into the portion of the anatomy of the patient; using a trained machine-learning model to determine a location of the distal end of the medical device in the input medical imaging data, wherein: the trained machine-learning model is trained, based on (i) training medical imaging data and training non-optical in vivo image data of at least a portion of an anatomy of one or more individuals and (ii) registration data associating the training non-optical in vivo image data with locations in the training medical imaging data as ground truth; the training is configured to cause the trained machine-learning model to learn associations between the training non-optical in vivo image data and the training medical imaging data, and the trained machine-learning model is configured to use the learned associations to determine the location of the distal end of the medical device in the input medical imaging data based on the input non-optical in vivo image data; modifying the input medical imaging data to include a location indicator indicative of the determined location of the distal end of the medical device; and causing a display to output the modified input medical imaging data including the location indicator.

In some embodiments, the input non-optical in vivo image data may include ultrasound data. In some embodiments, the portion of the anatomy of the patient may include a peripheral portion of a lung of the patient.

In a further aspect, an exemplary embodiment of a method of training a machine-learning model to determine an output location of a distal end of a medical device in an anatomy of a patient within input medical imaging data, in response to receiving the input medical imaging data and receiving, from a sensor positioned on the distal end of a medical device, input non-optical in vivo image data, may include: inputting training data into the machine-learning model, the training data including training medical imaging data and training non-optical in vivo image data of at least a portion of an anatomy of one or more individuals; inputting ground truth into the machine-learning model that includes registration data associating the training non-optical in vivo image data with locations in the training medical imaging data; and using the training data and the ground truth with the machine-learning model to learn associations between the training non-optical in vivo image data and the training medical imaging data that are usable by the machine-learning model to determine the output location of the distal end of the medical device.

In some embodiments, the method may further include using the training data and the ground truth with the machine-learning model to learn associations between a sequence of training non-optical in vivo images and a path of travel within the training medical imaging data, such that the machine learning-model is configured to determine the location of the distal end of the medical device in the input medical imaging data by predicting a path of travel of the distal end of the medical device from a previous location in the input medical imaging data using the input non-optical in vivo image data.

In some embodiments, the training non-optical in vivo image data is ultrasound data.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION OF EMBODIMENTS

Figure 1:
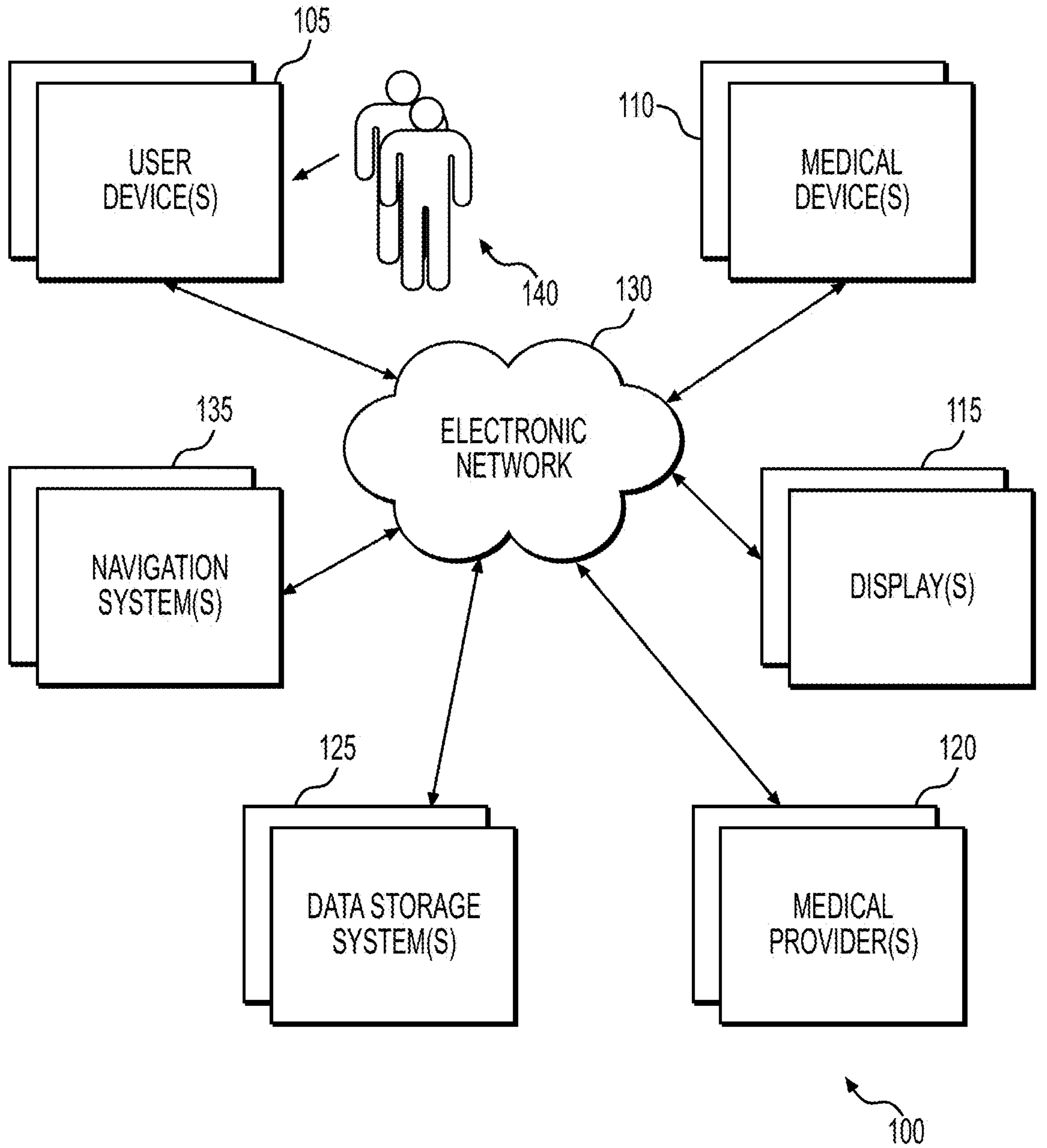
FIG. 1 depicts an exemplary environment for training and/or using a machine-learning model to provide in vivo navigation of a medical device, according to one or more embodiments.

According to certain aspects of the disclosure, methods and systems are disclosed for providing in vivo navigation of a medical device, e.g., an ablation device to be navigated within the periphery of a lung of a patient. In certain medical procedures, it may be desirable to navigate a medical device into a location within the body. However, conventional navigation techniques may not be suitable. For example, conventional techniques may not be sufficiently accurate for navigating to a target site and/or confirming that a target site has been reached. Conventional navigation techniques may also rely on inclusion of a light source, camera, and/or lens, which may result in a medical device of a size that may be too large to be navigated to some target sites.

As will be discussed in more detail below, in various embodiments, systems and methods are described for using machine learning to locate a distal end of a medical device, with reference to medical imaging data, e.g., pre-operative CT scan data, based on non-optical in vivo image data received from a sensor disposed on the distal end of the medical device. By training a machine-learning model, e.g., via supervised or semi-supervised learning, to learn associations between the non-optical in vivo image data and positions of the distal end of the medical device within the medical imaging data, the trained machine-learning model may be usable to provide navigation information for the medical device, e.g., a position indicator in the medical imaging data indicating a live location of the distal end of the medical device.

Reference to any particular procedure is provided in this disclosure only for convenience and not intended to limit the disclosure. A person of ordinary skill in the art would recognize that the concepts underlying the disclosed devices and methods may be utilized in any suitable procedure. The disclosure may be understood with reference to the following description and the appended drawings, wherein like elements are referred to with the same reference numerals.

The terminology used below may be interpreted in its broadest reasonable manner, even though it is being used in conjunction with a detailed description of certain specific examples of the present disclosure. Indeed, certain terms may even be emphasized below; however, any terminology intended to be interpreted in any restricted manner will be overtly and specifically defined as such in this Detailed Description section. Both the foregoing general description and the following detailed description are exemplary and explanatory only and are not restrictive of the features, as claimed.

For ease of description, portions of the device and/or its components are referred to as proximal and distal portions. It should be noted that the term "proximal" is intended to refer to portions closer to a user of the device, and the term "distal" is used herein to refer to portions further away from the user. Similarly, extends "distally" indicates that a component extends in a distal direction, and extends "proximally" indicates that a component extends in a proximal direction.

In this disclosure, the term "based on" means "based at least in part on." The singular forms "a," "an," and "the" include plural referents unless the context dictates otherwise. The term "exemplary" is used in the sense of "example" rather than "ideal." The terms "comprises," "comprising," "includes," "including," or other variations thereof, are intended to cover a non-exclusive inclusion such that a process, method, or product that comprises a list of elements does not necessarily include only those elements, but may include other elements not expressly listed or inherent to such a process, method, article, or apparatus. The term "or" is used disjunctively, such that "at least one of A or B" includes, (A), (B), (A and A), (A and B), etc. Relative terms, such as, "substantially" and "generally," are used to indicate a possible variation of ±10% of a stated or understood value.

As used herein, terms such as "medical imaging data" or the like generally encompass data associated with and/or indicative of a geometry and/or physiology of a patient, e.g., that may be generating via medical imaging and/or that may be represented as an image of the anatomy of the patient, e.g., a two-dimensional image, a three-dimensional image or model, a video, a time-varying image, etc. Medical imaging generally encompasses techniques whereby a signal (light, electromagnetic energy, radiation, etc.) is generated, and measurements are taken that are indicative of how that signal interacts with and/or is affected by, transmitted through, or the like, the patient. Examples of medical imaging technologies include CT scans, MRI scans, X-ray scans, or any other suitable modality, e.g., that may be used to visualize an interior of at least a portion of the patient's anatomy. Medical imaging data may include, for example, two-dimensional data and/or images, three-dimensional data and/or images, voxel data, a geometric model of at least a portion of patient anatomy, a solid model of the portion of patient anatomy, a mesh of nodes or points representative of the portion of the anatomy and/or characteristics of the portion of the anatomy, and/or any other suitable data associated with the patient and/or medical imaging.

As used herein, "non-optical image data" generally encompasses data that is indicative of, associated with, and/or usable to generate an image, and that was generated using a non-optical signal, e.g., via a signal generated by an ultrasound transducer.

As used herein, a "machine-learning model" generally encompasses instructions, data, and/or a model configured to receive input, and apply one or more of a weight, bias, classification, or analysis on the input to generate an output. The output may include, for example, a classification of the input, an analysis based on the input, a design, process, prediction, or recommendation associated with the input, or any other suitable type of output. A machine-learning model is generally trained using training data, e.g., experiential data and/or samples of input data, which are fed into the model in order to establish, tune, or modify one or more aspects of the model, e.g., the weights, biases, criteria for forming classifications or clusters, or the like. Aspects of a machine-learning model may operate on an input linearly, in parallel, via a network (e.g., a neural network), or via any suitable configuration.

The execution of the machine-learning model may include deployment of one or more machine learning techniques, such as linear regression, logistical regression, random forest, gradient boosted machine (GBM), deep learning, and/or a deep neural network. Supervised and/or unsupervised training may be employed. For example, supervised learning may include providing training data and labels corresponding to the training data. Unsupervised approaches may include clustering, classification or the like. K-means clustering or K-Nearest Neighbors may also be used, which may be supervised or unsupervised. Combinations of K-Nearest Neighbors and an unsupervised cluster technique may also be used. Any suitable type of training may be used, e.g., stochastic, gradient boosted, random seeded, recursive, epoch or batch-based, etc.

In certain medical procedures, it may be desirable to navigate a medical device to a target site within the body of a patient, e.g., into the periphery of a lung of the patient for a procedure such as ablation of undesirable tissue. However, conventional in vivo navigation techniques, e.g., conventional bronchoscope techniques, may not be sufficiently accurate for navigating to the target site, or verifying that the target site has been reached.

A concern for bronchoscopic techniques is the ability to not only accurately navigate to a target for ablation, but also to confirm that a target has been reached. Generally, during a procedure such as the above, medical imaging, such as a CT image of the patient taken prior or during a procedure, may be used as a passive map in conjunction with active navigation via a bronchoscope. Bronchoscopic techniques for such purpose include navigational (electromagnetic and/or video) bronchoscopy, radial-probe endobronchial ultrasound, and robotic bronchoscopy.

However, conventional navigation techniques, including the foregoing, fail to adequately address concerns of accurate navigation to and confirmation of a target. Electromagnetic navigation alone is generally insufficient to provide fine-grained detail and/or confirming that a target site is reached. Video navigation may be used to confirm arrival at a target site, but provides limited information, and moreover the requirement for a light source, camera, and lens with the bronchoscope may increase device diameter to a size that is too big to reach desired portions of the periphery of the lung. Radial probes require rotation of the device for imaging, which may present risks to the patient and/or may not be possible depending on the physiology of the patient and/or the position of the device. And, robotic bronchoscopy generally involves large and/or complex machines external to the patient operating in concert with the procedure, such as a CT imaging machine or the like, which can be cumbersome and/or costly. Conventional techniques may result in a medical device that is too large to navigate to the target site, that may present risk to the patient, and/or that may require large, complex, and/or expensive external machinery to operate in conjunction with the procedure. Accordingly, improvements in technology relating to in vivo navigation for a medical device are needed.

In the following description, embodiments will be described with reference to the accompanying drawings. As will be discussed in more detail below, in various embodiments, systems and methods for providing in vivo navigation of a medical device are described.

In an exemplary use case, a medical procedure includes introducing and/or advancing a medical device to a target site within a patient's body. Medical imaging, such as a CT scan or the like, may be taken of at least a portion of the patient's body that includes the target site, e.g., prior to and/or during the procedure. A location of the target site in the patient's body may be identified in the medical imaging. The medical device may be introduced into the patient's body so as to be advanced toward the target site. For example, the medical device may be introduced via the patient's airway so as to be advanced toward a target site in the patient's lung. The medical device may include an end effector, such as an ablation device, positioned on a distal end of the medical device, e.g., for performing a therapeutic procedure. The medical device may further include a sensor positioned on the distal end of the medical device, such as a transducer configured to generate a signal indicative of an ultrasound medical image. The medical device may, in some instances, not include one or more of a camera, a light source, or a lens. A navigation system may be configured to receive the signal generated by the sensor, e.g., receive non-optical in vivo image data from the sensor. The navigation system may include a trained machine-learning model that is configured to determine a location of the distal end of the medical device within the patient's body in the medical imaging data based on the received non-optical in vivo image data from the sensor. The navigation system may modify the medical imaging data so as to include a location indicator indicative of a location of the distal end of the medical device within the anatomy of the patient depicted by the medical imaging data, and may cause a display to output the modified medical imaging data. For example, the display may depict a live location of the distal end of the medical device within the medical imaging data as it travels within the anatomy of the patient.

In another exemplary use case, a machine-learning model may be trained to determine a location, within medical imaging data, of a distal end of a medical device advanced into anatomy of a patient. Training data that includes medical imaging data and non-optical in vivo image data of at least a portion of an anatomy of one or more individuals may be input into the machine-learning model. Ground truth that includes registration data associating the non-optical in vivo image data with locations in the medical imaging data may also be input into the machine-learning model. The training data and the ground truth may be used with the machine-learning model to develop associations between non-optical in vivo image data and medical imaging data usable by the machine-learning model to determine the output location of the distal end of the medical device.

In some instances, the ground truth may be at least partially developed with an additional navigation technique. For example, the training data and ground truth may be obtained using a medical device that includes a sensor, e.g., such as an ultrasound transducer, and that also includes an optical sensor such as a camera. Video bronchoscopy may be used to determine and/or verify a location of the medical device in order to generate a ground truth association between the signal from the sensor and a location of the medical device in the medical imaging data. Further, the training of the machine-learning model may be validated by comparing a location determined via the trained model with a location determined via the video bronchoscopy.

While several of the examples above involve ultrasound, it should be understood that techniques according to this disclosure may be adapted to any suitable type of non-optical imaging. In one example, a pressure sensor, medical imaging technique, or the like may be used to determine pressures, temperatures, or other biological or physiological characteristics within the body of a patient. A medical device may include, instead of or in addition to the sensor described above, a further sensor configured to sense one or more of such biological or physiological characteristics. The one or more determined characteristics within the body and the one or more determined characteristics sensed by the further sensor may be used as inputs for the machine-learning model. Further, while several of the examples above involve bronchoscopy and/or navigation in and/or ablation of tissue within the periphery of the lungs, it should be understood that techniques according to this disclosure may be adapted to any suitable procedure involving in vivo navigation of a medical device including, for example, a cardiac or heart valve procedure, any procedure in the pulmonary, gastrointestinal, urinary, or other body tract, any procedure using an endoscope, bronchoscope, colonoscope, ureteroscope, or other like devices, and/or any therapeutic or diagnostic procedure including, for example, biopsy, ablation, resection, dissection, injection, application of a drug or therapeutic, etc., or combinations thereof. It should also be understood that the examples above are illustrative only. The techniques and technologies of this disclosure may be adapted to any suitable activity.

Presented below are various aspects of machine learning techniques that may be adapted to in vivo navigation of a medical device. As will be discussed in more detail below, machine learning techniques adapted to determining a location and/or path of travel of a medical device within anatomy of a patient, with reference to medical imaging data, may include one or more aspects according to this disclosure, e.g., a particular selection of training data, a particular training process for the machine-learning model, operation of a particular device suitable for use with the trained machine-learning model, operation of the machine-learning model in conjunction with particular data such as medical imaging data, modification of such particular data by the machine-learning model, etc., and/or other aspects that may be apparent to one of ordinary skill in the art based on this disclosure.

FIG. 1 depicts an exemplary environment 100 that may be utilized with techniques presented herein. One or more user device(s) 105, one or more medical device(s) 110, one or more display(s) 115, one or more medical provider(s) 120, and one or more data storage system(s) 125 may communicate across an electronic network 130. As will be discussed in further detail below, one or more navigation system(s) 135 may communicate with one or more of the other components of the environment 100 across electronic network 130. The one or more user device(s) 105 may be associated with a user 140, e.g., a user associated with one or more of generating, training, or tuning a machine-learning model for providing in vivo navigation of a medical device, generating, obtaining, or analyzing medical imaging data, and/or performing a medical procedure.

In some embodiments, the components of the environment 100 are associated with a common entity, e.g., a hospital, facility, or the like. In some embodiments, one or more of the components of the environment is associated with a different entity than another. The systems and devices of the environment 100 may communicate in any arrangement. As will be discussed herein, systems and/or devices of the environment 100 may communicate in order to one or more of generate, train, or use a machine-learning model to provide in vivo navigation for the medical device 110, among other activities.

The user device 105 may be configured to enable the user 140 to access and/or interact with other systems in the environment 100. For example, the user device 105 may be a computer system such as, for example, a desktop computer, a mobile device, a tablet, etc. In some embodiments, the user device 105 may include one or more electronic application(s), e.g., a program, plugin, browser extension, etc., installed on a memory of the user device 105. In some embodiments, the electronic application(s) may be associated with one or more of the other components in the environment 100. For example, the electronic application(s) may include one or more of system control software, system monitoring software, software development tools, etc.

Figure 2A:
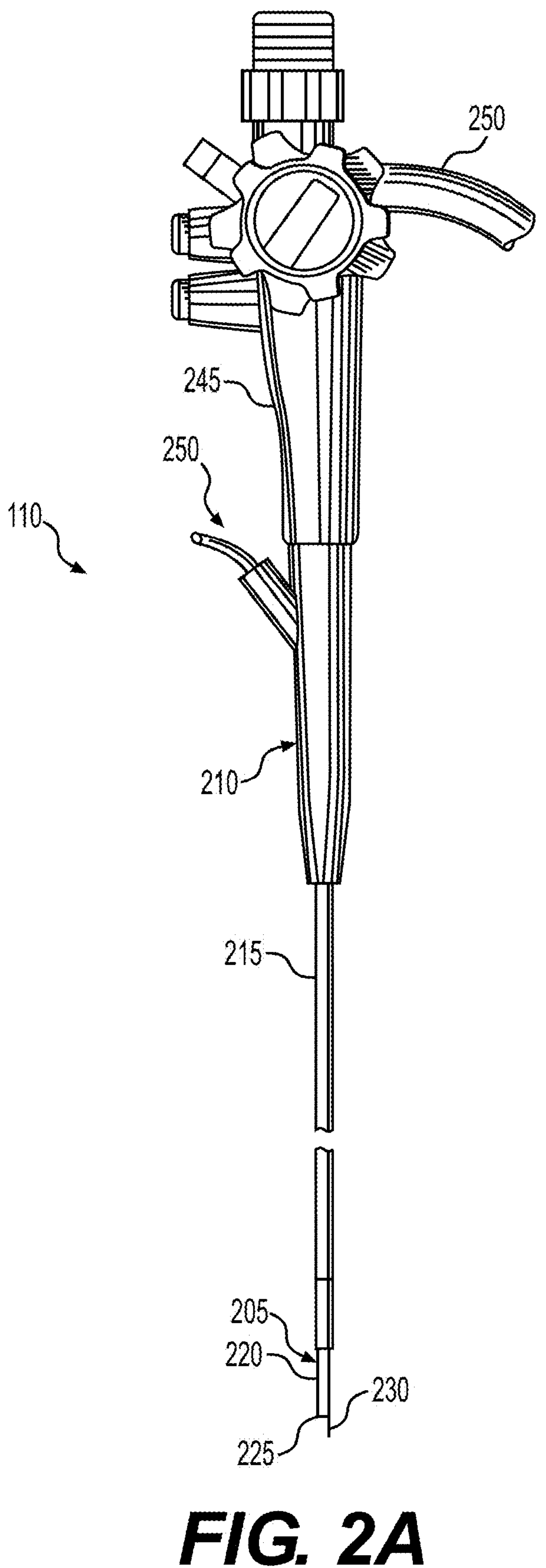
FIG. 2A depicts an exemplary embodiment of a medical device usable with the environment of FIG. 1, according to one or more embodiments.

FIG. 2A depicts an exemplary embodiment of the medical device 110. However, it should be understood that the embodiment in FIG. 2 is illustrative only, and that any suitable medical device for in vivo navigation to a target site may be used. The medical device 110 may include a distal end 205 connected to a proximal end 210 via a tube 215.

The distal end 205 may include one or more portions 220 configured to one or more of receive a component or communicate with a lumen disposed in the tube 215. For example, at least one sensor 225 may be disposed in one of the portions 220. In another example, a tool having an end effector 230 may be disposed in another of the portions 220, e.g., an ablation device, forceps, a net, an orifice for taking in or outputting fluid and/or material, etc. The sensor 225 may include, for example, a transducer, an electromagnetic position sensor, a fiber-optic position sensor, or the like. In the embodiment depicted in FIG. 2, the sensor 225 includes a transducer array, but it should be understood that any suitable type of non-optical sensor may be used.

The tube 215 may, in some embodiments, be formed from a flexible material. The tube 215 may include one or more lumens (not shown) that communicate between the distal end 205 and the proximal end 210. In some embodiments, the tube 215 may further include and/or house other elements such as a wire connector configured to communicate data between a component at the distal end 205, e.g., the sensor 225, and the proximal end 210.

The proximal end 210 may include, for example, a handle portion 245 that enable an operator to manipulate, advance, retract, and/or orient the distal end 205. The proximal end 210 may further include one or more interface 250, e.g., an umbilicus to output data, send or receive electrical signals, and/or communicate a fluid or material into or out from the medical device 110. An interface for data may include one or more of a wired or wireless connection. The interface 250 may also be configured to receive power for operating the sensor 225 or the end effector 230.

In this embodiment, the medical device 110 does not include a visual navigation element such as a fiber-optic line and lens, a camera, or the like. As a result, the distal end 205, and in some embodiments, the tube 215, may have an outer diameter that is small relative to a conventional medical device such as a bronchoscope. For example, the medical device 110 may have an outer diameter suitable for navigation into a periphery of a lung, e.g., a diameter of 3 millimeters or less.

In some embodiments, the medical device 110, or at least a portion thereof, is configured to be disposable, e.g., a single-use device. By not including a visual navigation element, a cost due to disposal of the medical device 110 may be reduced relative to conventional medical devices.

Referring again to FIG. 1, the display 115 may be configured to output information received from other systems in the environment 100. For example, the display 115 may be a monitor, a tablet, a television, a mobile device, etc. In some embodiments, the display 115 may be integrated into another component of the environment, e.g., the user device 105.

The medical provider 120 may include and/or represent a person using a computer system, the computer system, and/or an entity that uses the computer system. For example, the medical provider 120 may include a medical imaging device such as a CT scanner, an entity such as a hospital or outpatient facility that uses a medical imaging device, a medical data exchange system, or the like. The medical provider 120 may generate or otherwise obtain medical imaging data, e.g., by performing medical imaging on a patient and/or perform analysis of the obtained medical imaging data. For example, the medical provider 120 may perform a CT scan on a patient, and generate a three-dimensional model and/or two-dimensional image of at least a portion of an anatomy of the patient. The medical provider 120 may also obtain any suitable patient-specific information, such as age, medical history, etc. The medical provider 120 may provide and/or provide access to medical imaging data and/or any other data to one or more of the other components of the environment 100, e.g., the navigation system 135 as discussed in further detail below.

The data storage system 125 may include a server system, an electronic medical data system, computer-readable memory such as a hard drive, flash drive, disk, etc. In some embodiments, the data storage system 125 includes and/or interacts with an application programming interface for exchanging data to other systems, e.g., one or more of the other components of the environment. The data storage system 125 may include and/or act as a repository or source for medical imaging data. For example, medical imaging data resulting from a CT scan may be stored by the data storage system 125 and/or provided by the data storage system 125 to the navigation system 135 as discussed in more detail below.

In various embodiments, the electronic network 130 may be a wide area network ("WAN"), a local area network ("LAN"), personal area network ("PAN"), or the like. In some embodiments, electronic network 130 includes the Internet, and information and data provided between various systems occurs online. "Online" may mean connecting to or accessing source data or information from a location remote from other devices or networks coupled to the Internet. Alternatively, "online" may refer to connecting or accessing an electronic network (wired or wireless) via a mobile communications network or device. The Internet is a worldwide system of computer networks—a network of networks in which a party at one computer or other device connected to the network can obtain information from any other computer and communicate with parties of other computers or devices. The most widely used part of the Internet is the World Wide Web (often-abbreviated "WWW" or called "the Web"). A "website page" generally encompasses a location, data store, or the like that is, for example, hosted and/or operated by a computer system so as to be accessible online, and that may include data configured to cause a program such as a web browser to perform operations such as send, receive, or process data, generate a visual display and/or an interactive interface, or the like.

As discussed in further detail below, the navigation system 135 may one or more of (i) generate, store, train, or use a machine-learning model configured to determine a location of the distal end 205 of the medical device 110, adjust medical imaging data for a patient, e.g., based on a determined location of the distal end 205, to include a visual indicator of that location, operate the display 115 to display the adjusted medical imaging data, among other activities. The navigation system 135 may include a machine-learning model and/or instructions associated with the machine-learning model, e.g., instructions for generating a machine-learning model, training the machine-learning model, using the machine-learning model etc. The navigation system 135 may include instructions for retrieving medical imaging data, adjusting medical imaging data, e.g., based on the output of the machine-learning model, and/or operating the display 115 to output medical imaging data, e.g., as adjusted based on the machine-learning model. The navigation system 135 may include training data, e.g., medical imaging data and non-optical in vivo image data from one or more individuals, and may include ground truth, e.g., registration data associating the non-optical in vivo image data with locations in the medical imaging data.

In some embodiments, the non-optical image data includes ultrasound data. Ultrasound data generally includes data associated with the internal structure of a portion of the patient's anatomy that was generated via the application of ultrasound to the anatomy of the patient, whereby pulses of high frequency vibration are transmitted into tissue using a probe, e.g., an ultrasound transducer. The vibrations reflect, at least partially, from surfaces that represent a change in acoustic impedance within the body, e.g., a geometry of a structure or tissue. Reflected vibrations that return to the transducer may be transmitted, e.g., via a wire in the tube 215 to a connector on the proximal end 210 and/or to the medical provider system 120 for processing into image data. The generation of the image data is based on the time taken by the reflections to return to the transducer after application of the vibrations, and the intensity of the returned reflections. A conventional transducer generally is configured to receive variance in signal response across only one dimension. In other words, for a static location of a transducer, only one column of pixel data for an ultrasound image may be received. Thus, in order to generate an image, the transducer is generally swept over a field of view, e.g., rotated back and forth, in order to successively add and/or refresh columns of values to the data.

Figure 2B:
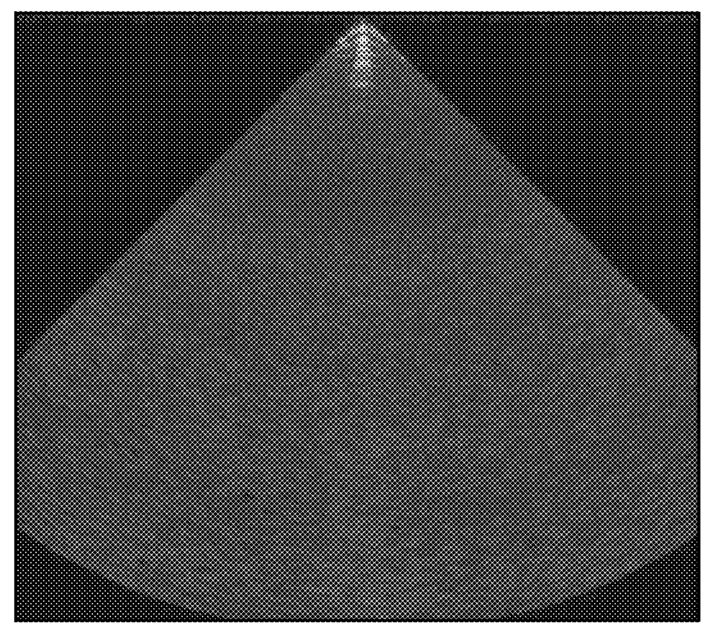
FIG. 2B depicts an exemplary ultrasound image produced by a transducer operating in air.
Figure 2C:
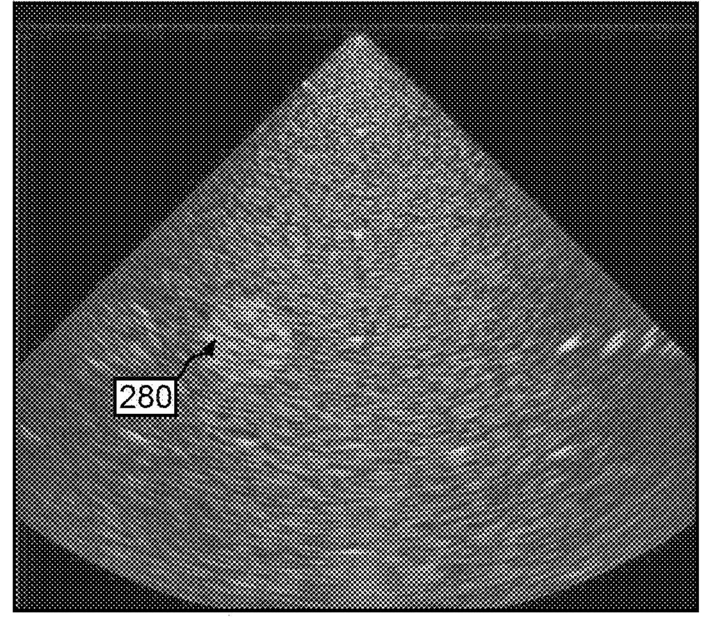
FIG. 2C depicts another exemplary ultrasound image produced by a transducer operating in vivo with a gap between the transducer and surrounding tissue.

Because the data is gathered based on received reflections, generally, in order to receive a signal at a location, the transducer must be in contact with the surrounding tissue. However, this may not always be the case, especially when the medical device has a diameter smaller than the size of the anatomy in which it is navigating. An air or gaseous gap or the like due to the transducer and the surrounding tissue generally results in the signal from the transducer being reflected back. FIG. 2B depicts an exemplary ultrasound image for a transducer operating in air, such that an essentially blank ultrasound image is formed. FIG. 2C depicts an exemplary ultrasound image for a transducer operating in an airway whereby a gap exists between the transducer and surrounding tissue over at least a portion of the sweep of the transducer. This gap results in an artifact 280 in the image data known as a "ringdown" artifact, which is generally considered to reduce the diagnostic use of the image data. However, image data, even with the presence of such artifacts, may be used for the purpose of navigation. For example, the presence of a ringdown artifact may be an indication that the diameter of the lumen in which the medical device is travelling is too large for the device, which may operate as an indication that the device may not have been advanced sufficiently into the periphery of the lung where lumen diameters decrease. Further uses for such imaging data is discussed in more detail below, As noted above, in some embodiments, the medical device 110 includes a transducer array. A transducer array may include, for example, a plurality of transducers arranged in parallel with each other, e.g., distributed over at least a portion of an outer circumference of the distal end. As a result, multiple columns of data may be sensed at once without rotation of the sensor 225. In various embodiments, any suitable transducers in parallel may be used. Additional transducers effectively increases the static field of view of the sensor 225. In various embodiments, the sensor 225, the medical device 110, and/or another system are configured to control the acquisition of data using a sensor with transducers in parallel and/or control the combining of signals from the parallel transducers into combined medical imaging data.

In some embodiments, a system or device other than the navigation system 135 is used to generate and/or train the machine-learning model. For example, such a system may include instructions for generating the machine-learning model, the training data and ground truth, and/or instructions for training the machine-learning model. A resulting trained-machine-learning model may then be provided to the navigation system 135.

Generally, a machine-learning model includes a set of variables, e.g., nodes, neurons, filters, etc., that are tuned, e.g., weighted or biased, to different values via the application of training data. In supervised learning, e.g., where a ground truth is known for the training data provided, training may proceed by feeding a sample of training data into a model with variables set at initialized values, e.g., at random, based on Gaussian noise, a pre-trained model, or the like. The output may be compared with the ground truth to determine an error, which may then be back-propagated through the model to adjust the values of the variable.

Training may be conducted in any suitable manner, e.g., in batches, and may include any suitable training methodology, e.g., stochastic or non-stochastic gradient descent, gradient boosting, random forest, etc. In some embodiments, a portion of the training data may be withheld during training and/or used to validate the trained machine-learning model, e.g., compare the output of the trained model with the ground truth for that portion of the training data to evaluate an accuracy of the trained model. The training of the machine-learning model may be configured to cause the machine-learning model to learn associations between non-optical in vivo image data and medical imaging data, such that the trained machine-learning model is configured to determine an output location within input medical imaging data in response to the input medical imaging data and input non-optical in vivo image data based on the learned associations.

As noted above, the machine-learning model may be configured to receive as input medical imaging data and non-optical in vivo image data. Such data may generally be expressed as an array of pixels or voxels. For example, a monochromatic two-dimensional image may be represented as a two-dimensional array of values corresponding to intensities of pixels of the image. Three-dimensional imaging data, e.g., resulting from a CT scan or the like, may be represented as a three-dimensional array. The variables of the machine-learning model perform operations on the input data in order to generate an output. The output, as noted above, may be a location within the medical imaging data, e.g., three-dimensional coordinates or data indicative thereof. It should be understood that the number of dimensions of the foregoing data is exemplary, and that any suitable type of data may be used. e.g., data that has a time component.

In various embodiments, the variables of a machine-learning model may be interrelated in any suitable arrangement in order to generate the output. For example, in some embodiments, the machine-learning model may include image-processing architecture that is configured to identify, isolate, and/or extract features, geometry, and or structure in one or more of the medical imaging data and/or the non-optical in vivo image data. For example, the machine-learning model may include one or more convolutional neural network ("CNN") configured to identify features in the medical imaging data and/or the non-optical in vivo image data, and may include further architecture, e.g., a connected layer, neural network, etc., configured to determine a relationship between the identified features in order to determine a location in the medical imaging data.

In some instances, different samples of training data and/or input data may not be independent. For example, as the distal end 205 of the medical device 110 moves within the anatomy of a patient, the non-optical in vivo image data sensed by the sensor 225 at a current location may be related to the non-optical in vivo image data sensed by the sensor 225 at a previous location. In other words, factors such as one or more of the geometric characteristics of the patient's anatomy and the successive travel of the distal end 225 may result in the non-optical in vivo image data sensed by the sensor 225 as successive instances to be related. Thus, in some embodiments, the machine-learning model may be configured to account for and/or determine relationships between multiple samples.

For example, in some embodiments, the machine-learning model of the navigation system 135 may include a Recurrent Neural Network ("RNN"). Generally, RNNs are a class of feed-forward neural networks that may be well adapted to processing a sequence of inputs. In some embodiments, the machine-learning model may include a Long Shor Term Memory ("LSTM") model and/or Sequence to Sequence ("Seq2Seq") model. An LSTM model may be configured to generate an output from a sample that takes at least some previous samples and/or outputs into account. A Seq2Seq model may be configured to, for example, receive a sequence of non-optical in vivo images as input, and generate a sequence of locations, e.g., a path, in the medical imaging data as output.

Although depicted as separate components in FIG. 1, it should be understood that a component or portion of a component in the environment 100 may, in some embodiments, be integrated with or incorporated into one or more other components. For example, a portion of the display 115 may be integrated into the entity user device 105 or the computer system associated with a medical provider 120. In another example, the navigation system 135 may be integrated with the medical provider system 120 and/or the data storage system 125. In some embodiments, operations or aspects of one or more of the components discussed above may be distributed amongst one or more other components. Any suitable arrangement and/or integration of the various systems and devices of the environment 100 may be used.

Further aspects of the machine-learning model and/or how it may be utilized in conjunction with a medical device 110 and/or a medical procedure to navigate the medical device to a target site within a patient's anatomy are discussed in further detail in the methods below. In the following methods, various acts may be described as performed or executed by a component from FIG. 1, such as the navigation system 135, the user device 105, the medical device 110, the display 115, the medical provider system 120, or components thereof. However, it should be understood that in various embodiments, various components of the environment 100 discussed above may execute instructions or perform acts including the acts discussed below. An act performed by a device may be considered to be performed by a processor, actuator, or the like associated with that device. Further, it should be understood that in various embodiments, various steps may be added, omitted, and/or rearranged in any suitable manner.

Figure 3:
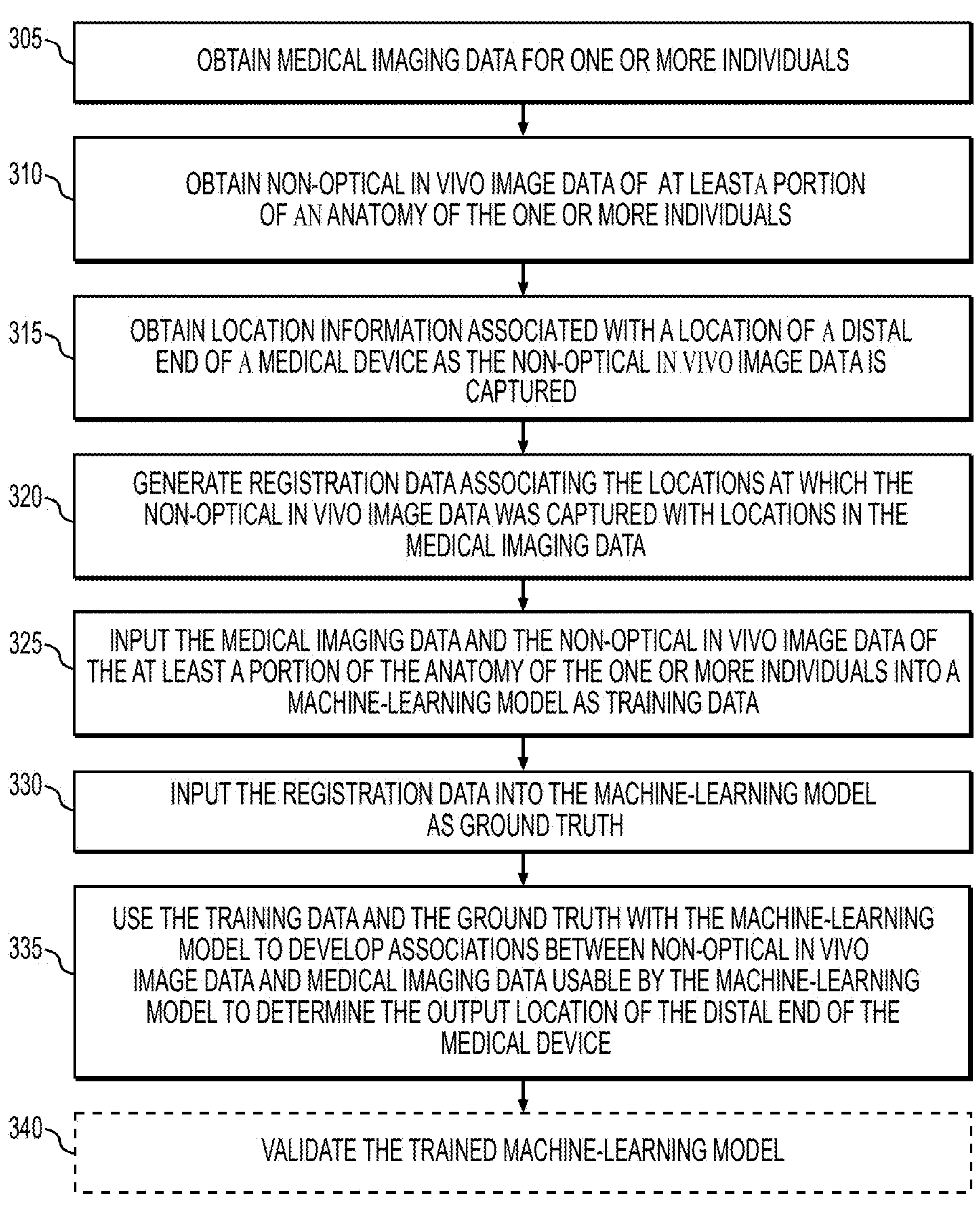
FIG. 3 depicts a flowchart of an exemplary method of training a machine-learning model to provide in vivo navigation of a medical device, according to one or more embodiments.

FIG. 3 illustrates an exemplary process for training a machine-learning model to determine an output location of a distal end 205 of a medical device 110 in an anatomy of a patient within first medical imaging data in response to input of the first medical imaging data and input of first non-optical in vivo image data received from a sensor positioned on the distal end of a medical device, such as in the various examples discussed above. At step 305, the medical provider 120 may obtain medical imaging data for one or more individuals. For example, the medical provider 120 may perform a CT scan of a portion of the one or more individuals' anatomy, e.g., the peripheral portion of the individuals' lungs, and or may retrieve such medical imaging data from another source, e.g., the data storage system

115, or another entity such as a hospital or outpatient facility, e.g., via an electronic medical database. In some embodiments, the individuals may be categorized based on one or more criteria, e.g., age, gender, height, weight, and/or any other suitable demographic data. In some embodiments, the individuals may not be human. For example, training data may be generated from animal studies using species with at least some anatomical similarity to humans, e.g., pigs or the like. Generally, the obtained medical imaging data is usable to depict a visual representation of the portion of the anatomy of each individual.

At step 310, the medical provider 120 may obtain non-optical in vivo image data of the at least portion of the anatomy of the one or more individuals. For example, the medical provider 120, e.g., a physician or operator or the like, may introduce a medical device, e.g., the medical device 110 or the like, into the body of the one or more individuals, and capture non-optical in vivo image data as a distal end of the medical device is navigated to a target site within a respective individual.

In some embodiments, the non-optical in vivo image data is ultrasound data. In some embodiments, the medical device includes a transducer array, such that the ultrasound data is received without requiring sweeping or rotation of the distal end. In some embodiments, the non-optical in vivo image data includes image data associated with at least a portion of a circumference of an interior of the anatomy. For example, in some embodiments, the field of view of the non-optical in vivo image data may be 30 degrees, 90 degrees, 180 degrees, 360 degrees, etc. In some embodiments, the transducer array is configured to continuously capture data, e.g., such that a continuous sequence of data values is captured for each segment of the transducer array as the transducer array travels within the anatomy of the individual.

At step 315, the medical provider 120 may obtain location information associated with a location of the distal end of the medical device as the non-optical image data is captured. Any suitable type of location information may be used. In some embodiments, the distal end of the medical device 110 may include an electromagnetic position sensor, e.g., that uses one or more electromagnetic signals to determine a three-dimensional location of the position sensor. In some embodiments, the distal end of the medical device may include an optical navigation element, e.g., a camera, optical fiber, lens, or the like, that enables the medical provider 120 to visually inspect the location of the distal end of the medical device within the anatomy of the patient, and enter such data, e.g., via a user device 105. In some embodiments, the medical device 110 may include a fiber optic shape sensing mechanism. In some embodiments, the location information includes shape information associated with a shape of the medical device 110. In some embodiments, an external scanner, e.g., a CT scanner, X-ray scanner, or the like, may be operated in conjunction with the travel of the medical device within the individual, and may be used to determine a location of the distal end within the individual. It should be understood that, while the medical device in this method may utilize some of the aforementioned optical navigation elements and techniques for the purpose of generating training data, as discussed in further detail below, there is no requirement that such elements or techniques are used during a procedure using a trained machine-learning model, even when training data used to train the model was collected with a medical device using optical navigation.

In some embodiments, the medical provider 120 may obtain additional data in addition to and/or based on the medical imaging data and/or non-optical in vivo image data. For example, in some embodiments, the medical provider 120 may extract at least one three-dimensional structure from the medical imaging data and/or the non-optical in vivo imaging data. For example, the medical provider 120 may generate a three-dimensional model based on the medical imaging data.

At step 320, the navigation system 135 may receive the obtained medical imaging data, non-optical in vivo image data, the location information, and optionally the additional data, and may generate registration data associating the locations at which the non-optical in vivo image data was captured with locations in the medical imaging data. In some embodiments, generating the registration data may include registering the anatomy of the individual with the medical imaging data and/or the generated three-dimensional model, and then associating the location at which the non-optical in vivo image data was captured with a corresponding location in the registered medical imaging data. In some embodiments, the medical provider may register a location of a structure extracted from the medical imaging data with a similar structure extracted from the non-optical in vivo imaging data. Any suitable measure of structural similarity may be used. In some embodiments, the medical provider 120 may be configured to receive user input, e.g., to set, adjust, or fine tune location information relative to the medical imaging data. For example, in some embodiments, the display 115 may output the medical imaging data in conjunction with the output of the optical navigation element, and enable the user to set, select, adjust, or tune a location for the current position of the distal end of the medical device in the medical imaging data. In some embodiments, the shape of the medical device 110 may be registered with geometry of the medical imaging data. The foregoing are examples only, and any suitable technique for registering the medical imaging data and the non-optical in vivo image data using the location information may be used.

At step 325, the navigation system 135 may input the medical imaging data and the non-optical in vivo image data of the at least a portion of the anatomy of the one or more individuals into a machine-learning model as training data. In some embodiments, the training data is inputted in batches. In some embodiments, at least a portion of the training data is withheld from the machine-learning model to be used as validation data. In some embodiments, training data is input as a respective sequence corresponding to each one of the one or more individual.

At step 330, the navigation system 135 may input the registration data into the machine-learning model as ground truth. In some embodiments, step 330 is performed concurrently, in parallel, or in sequence, e.g., alternatingly, with step 325.

At step 335, the navigation system 135 may use the training data and the ground truth with the machine-learning model to develop associations between non-optical in vivo image data and medical imaging data usable by the machine-learning model to determine the output location of the distal end of the medical device. For example, the navigation system 135 may, e.g., for each sample of training data, batch of training data, or the like, use the machine-learning model to determine an error between the training data and the ground truth, and back-propagate the error in order to adjust one aspect of the machine-learning model. By adjusting the aspects, e.g., variables, weights, biases, nodes, neurons, etc., of the machine-learning model, the machine-learning model is trained to learn the associations between non-optical in vivo image data and medical imaging data usable by the machine-learning model to determine the output location of the distal end of the medical device.

In some embodiments, by learning the associations, the machine-learning model may be configured to determine the location of the distal end 205 of the medical device 110 in the first medical imaging data by predicting a path of travel of the distal end 205 of the medical device 110 from a previous location in the first medical imaging data using the first non-optical in vivo image data. For example, in some embodiments, the machine-learning model and/or the navigation system 135 may be configured to track and or store the location(s) of the distal end 205 over time and/or determine the current location of the distal end 205 based on the previous location(s). In an exemplary embodiment, the machine-learning model may include one or more of a long short term memory network or a sequence-to-sequence model, e.g., as discussed in one or more of the examples above.

In some embodiments, the machine-learning model is configured to learn associations between the shape of the medical device 110, e.g., as the shape changes over time as the medical device 110 is moved, and a position of the distal end 205 within the medical imaging data.

In some embodiments, the machine-learning model is configured to learn associations between a sequence of dimensions or measurements, e.g., diameters such as cross-sectional diameters of a body lumen, determined based on of the non-optical in vivo image data and a path of travel within the medical imaging data. For example, in some embodiments, the medical provider 120 and/or the navigation system 135 may determine diameters at the locations in the medical imaging data, and/or may determine diameters for the non-optical in vivo image data, and may use such determined diameters as further inputs to the machine-learning model. In some embodiments, diameters of the locations in the medical imaging data may be determined based on a geometry of the portion of the anatomy associated with the medical imaging data. In some embodiments, the diameters of the locations in the medical imaging data and the non-optical in vivo image data are used as training data and the determined diameters of the locations are used as ground truth for the machine-learning model and/or another machine-learning model that is configured to output diameters in response to input of non-optical in vivo image data. Any suitable technique for determining diameters for interior portions of the anatomy based on non-optical in vivo image data may be used. While some of the embodiments above relate to diameters, it should be understood that, in at least some embodiments, the dimensions or measurements are not limited to circles or approximations of circles, and that any suitable dimension, measurement, and/or geometry may be used.

Optionally, at step 340, the navigation system 135 may validate the trained machine-learning model. For example, the navigation system 135 may input training data, e.g., a portion of the training data withheld from the machine-learning model during training, as validation data and use the trained machine-learning model to generate output location(s) of within the medical imaging data. The navigation system 135 may then compare locations of the generated output with the locations from the registration data of the ground truth corresponding to the input validation data to generate an accuracy of the trained machine-learning model. For example, the navigation system 135 may determine an accuracy based on an average distance between each location in the output and a corresponding location in the registration data. Any suitable accuracy measure may be used. The navigation system 135 may validate or reject the training of the machine-learning model based on whether the accuracy is above or below a predetermined threshold, respectively.

FIG. 4 illustrates an exemplary process for providing in vivo navigation of a medical device, e.g., by utilizing a trained machine-learning model such as a machine-learning model trained according to one or more embodiments discussed above. At step 405, the navigation system 135 may receive first medical imaging data associated with at least a portion of an anatomy of a patient. The first medical imaging data may be associated with a CT scan of the patient, or the like. The first medical imaging data may be received from a data storage system 125. For example, the first medical imaging data may have been obtained, e.g., via medical imaging of the patient, at a previous time, e.g., pre-operatively. The first medical imaging data may be received from a medical provider 120, e.g., from a medical imaging scanning device such as a CT scanner or the like that is operated in conjunction with the method. The at least portion of the anatomy may be a periphery of a lung of the patient. The first medical imaging data may identify a target site within the anatomy of the patient, e.g., a location of undesirable tissue to be ablated, a location of an illness or malady such as a lesion, a foreign mass, or any other suitable medically relevant location.

At step 410, the medical provider 120 may insert a distal end 205 of a medical device 110 into the body of the patient, and advance the distal end 205 toward the target site. For example, the medical provider 120 may insert the distal end 205 into the body of the patient, bronchially, endoscopically, laparoscopically, or via any other suitable technique.

At step 415, the navigation system 135 may receive first non-optical in vivo image data from a sensor positioned on the distal end 205 of the medical device 110. The first non-optical in vivo image data may include ultrasound data. The sensor may include an ultrasound transducer. The ultrasound transducer may be a transducer array. The first non-optical in vivo image data may include non-optical image data that extends over a sweep of a circumference, e.g., that has a field of view of 30 degrees, 90 degrees, 180 degrees, 360 degrees, etc., such that the field of view may be obtained without sweeping or rotating the sensor. The first non-optical image data may be received, for example, via an interface on a proximal end 210 of the medical device 110.

Optionally. at step 420, the navigation system 135 may receive a position signal from a position sensor positioned proximate to the distal end 205 of the medical device 110, e.g., via the interface. The position signal may include information usable to localize a location of the positon sensor to a predetermined region. For example, the position signal may include three-dimensional location information accurate to about six inches, three inches, one inch, etc. In various embodiments, the position sensor may include, for example, an electromagnetic position sensor, a fiber optic shape sensing mechanism, or the like, or combinations thereof. In some embodiments, the position signal includes information associated with a shape of the medical device 110, or the like.

Optionally, at step 425, the navigation system 135 may extract one or more three-dimensional structure from one or more of the first medical imaging data or the first non-optical in vivo image data. In some embodiments, the data received at step 405 may include one or more extracted structure, e.g., a geometrical three-dimensional model of the anatomy of the patient, or the like. In some embodiments, the extracted structure(s) includes a diameter of an interior portion of the anatomy of the patient.

At step 430, the navigation system 135 may use a trained machine-learning model, e.g., a model trained according to the method of FIG. 3 and/or other embodiments discussed above, to determine a location of the distal end 205 of the medical device 110 in the first medical imaging data. For example, the trained machine-learning model may have been trained, based on (i) second medical imaging data and second non-optical in vivo image data of at least a portion of an anatomy of one or more individuals as training data and (ii) registration data associating the second non-optical in vivo image data with locations in the second medical imaging data as ground truth. The training may have been configured to cause the trained machine-learning model to learn associations between non-optical in vivo image data and medical imaging data, such that the trained machine-learning model is configured to determine an output location within input medical imaging data in response to the input medical imaging data and input non-optical in vivo image data based on the learned associations. In some embodiments, the trained machine-learning model includes one or more of a long short term memory network or a sequence-to-sequence model.

In some embodiments, the navigation system 135 may use the position signal to localize a position of the distal end of the medical device to a region within the portion of the anatomy of the patient. In some embodiments, the navigation system 135 restricts the first medical imaging data input into the trained machine-learning model to only the localized region. In some embodiments, the navigation system 135 inputs the localized region as a further input of the trained-machine-learning model. In some embodiments, the trained machine-learning model is further configured to receive the position signal as an input. In some embodiments, the position signal includes one or more of a three-dimensional co-ordinate, a three-dimensional region or volume, a shape of the medical device 110, e.g., associated with a fiber optic shape sensor, etc.

In some embodiments, the navigation system 135 is configured to register at least one structure extracted from the first non-optical in vivo image data with geometry of the at least portion of the anatomy of the patient in the first medical imaging data, e.g., with at least one structure extracted from the first medical imaging data. In some embodiments, the determination of the location of the distal end 205 of the medical device 110 is further based on the registration of the at least one three-dimensional structure with the geometry. For example, the registration and/or the one or more extracted structure(s) may be used as further input(s) to the trained machine-learning model. In another example, the registration may be used to identify a localized region of the anatomy for determining the location.

In some embodiments, the trained machine-learning model was trained to learn associations between non-optical in vivo image data and dimensions or measurements, e.g., diameters of interior portions of anatomy. In some embodiments, the navigation system 135 may use the trained machine-learning model to determine a diameter of an interior portion of the anatomy of the patient at a current location of the distal end 205 of the medical device 110. In some embodiments, the navigation system 135 may compare the current diameter with geometry of the medical imaging data to identify a location in the medical imaging data matching the determined diameter, e.g., in order to determine the location of the distal end 205 of the medical device 110.

In some embodiments, the trained machine-learning model was trained to learn associations between a sequence of non-optical in vivo images of the non-optical in vivo image data and a path of travel within the medical imaging data. In some embodiments, the trained machine learning-model is configured to determine the location of the distal end 205 of the medical device 110 in the first medical imaging data by predicting a path of travel of the distal end 205 of the medical device from a previous location in the first medical imaging data using the first non-optical in vivo image data. For example, in some embodiments, the trained machine-learning model may be configured to accept the first medical imaging data and a sequence of non-optical in vivo images in the first non-optical in vivo imaging data as input, and generate a sequence of locations, e.g., a path, in the first medical imaging data as output.

In some embodiments, the trained machine-learning model was trained to learn associations between a sequence of dimensions or measurements such as diameters, e.g., that were determined based on the non-optical in vivo image data, and a path of travel within the medical imaging data. The trained machine-learning model may be configured to determine the location of the distal end 205 of the medical device 110 in the first medical imaging data by predicting sequence indicative of a path of travel of the distal end 205 of the medical device 110 from a previous location in the first medical imaging data using the first non-optical in vivo image data.

At step 435, the navigation system 135 may modify the first medical imaging data to include a location indicator indicative of the determined location of the distal end of the medical device. In various embodiments, the location indicator may include one or more of a graphic or object indicative of a location of the distal end 205, e.g., a geometric shape such as an arrow, circle, etc., a graphic or object indicative of a path of the distal end 205, e.g., a solid line, dashed line, coloration of portion(s) of the first medical imaging data that has been passed through, etc. In some embodiments, the location indicator includes a representation of the medical device 110 and/or the distal end 205 within the medical imaging data. In some embodiments, the first medical imaging data may be further adjusted to include a depiction of at least one structure extracted from one or more of the first medical imaging data or the first non-optical in vivo imaging data. In some embodiments, the first medical imaging data may be further adjusted to include a rendering or three-dimensional model of the anatomy of the patient at the current location of the distal end 205. In some embodiments, the first medical imaging data may be further adjusted to include an image generated based on the first non-optical in vivo image data. In some embodiments, first medical imaging data may be further adjusted to include a visual depiction of additional data, such as a distance between the distal end 205 and the target site or a confirmation that the target site has been reached by the distal end 205, e.g., as determined by the navigation system 135.

At step 440, the navigation system 135 may cause the display 115 to output the modified first medical imaging data including the location indicator. For example, the display 115 may show the first medical imaging data as a map of the anatomy of the patient, with the location indicator identifying the current location of the distal end 205 of the medical imaging device.

Figure 4A:
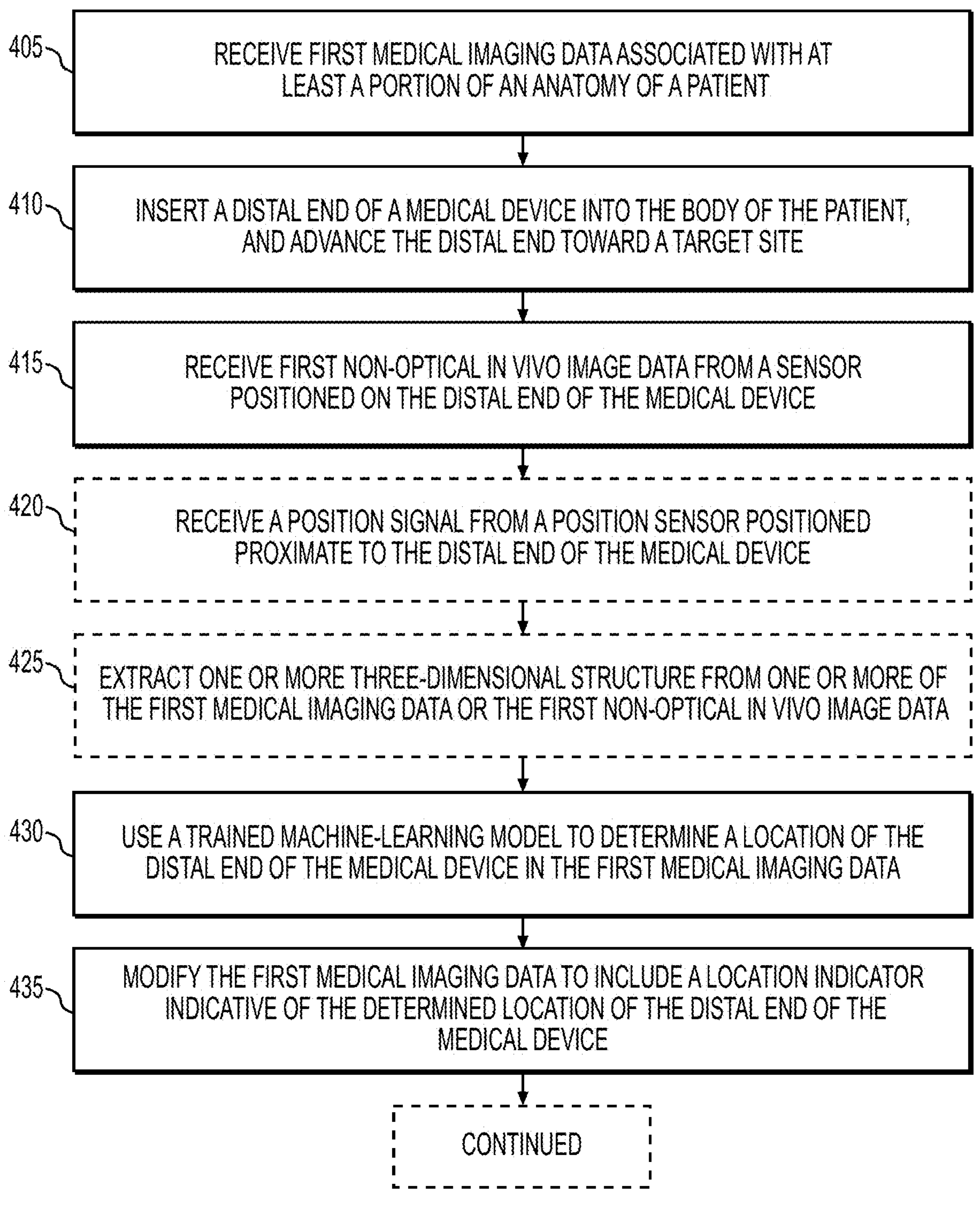
FIG. 4A depicts a flowchart of an exemplary method of using a trained machine-learning model to provide in vivo navigation of a medical device, according to one or more embodiments.
Figure 4A:
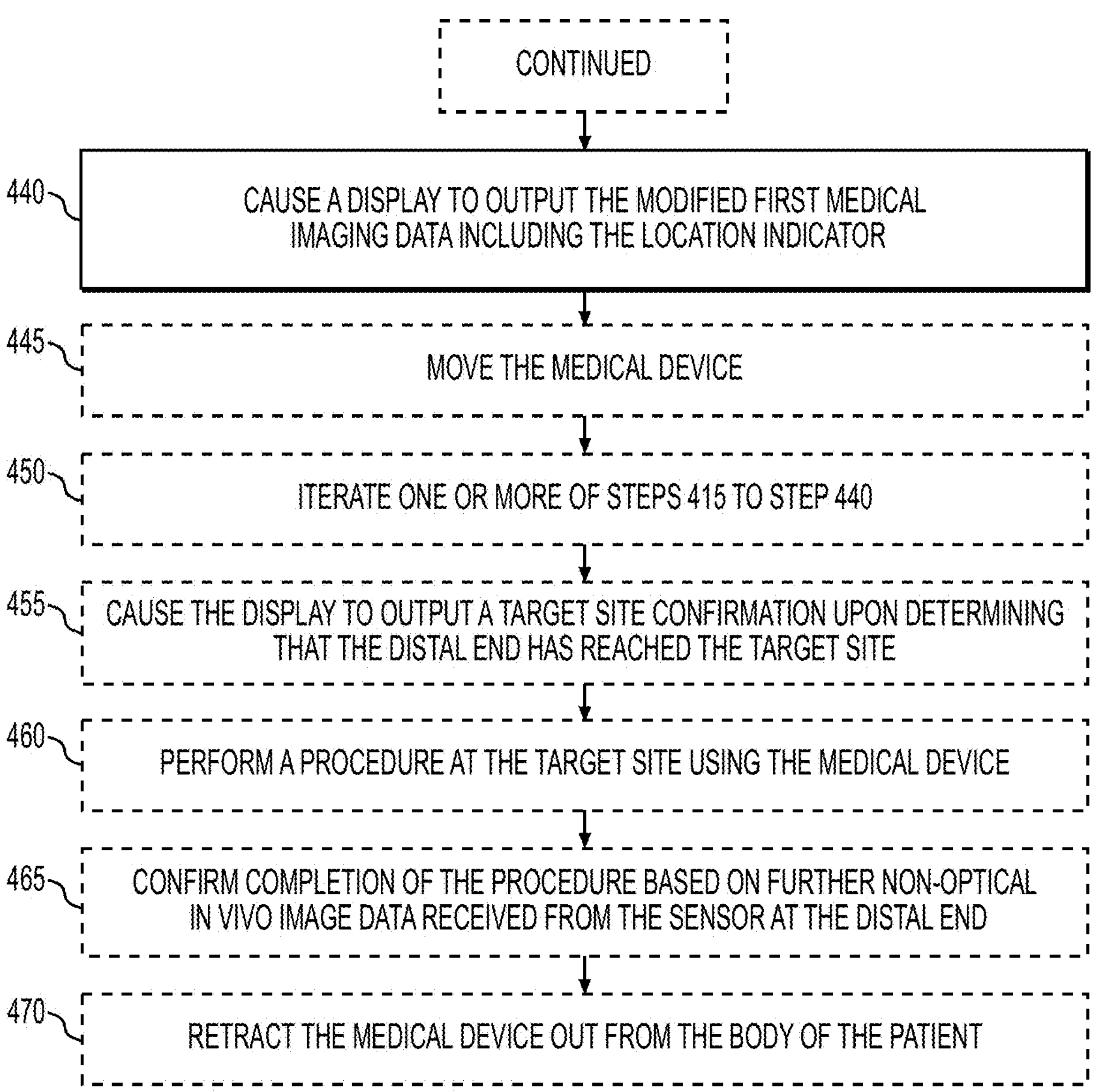
Figure 4B:
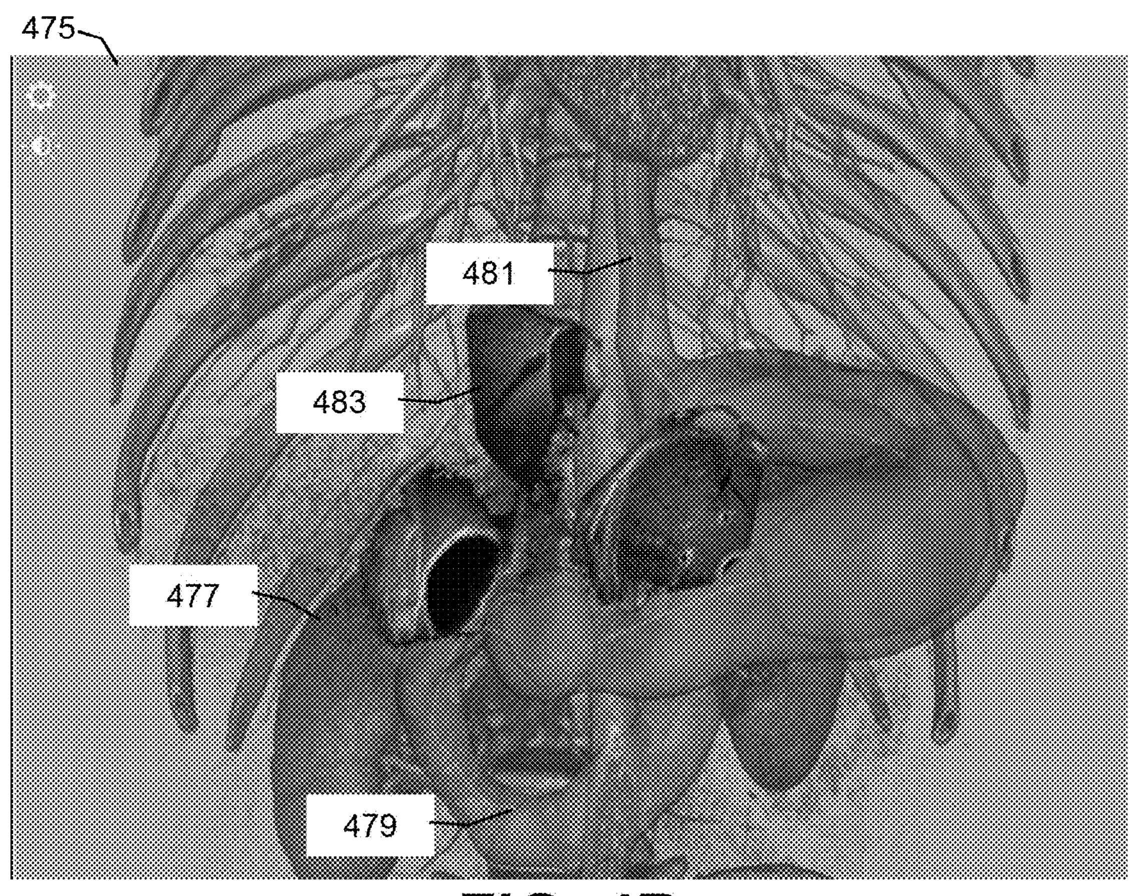
FIGS. 4B and 4C depict exemplary embodiments of a navigational output generated by a navigation system, according to one or more embodiments.
Figure 4C:
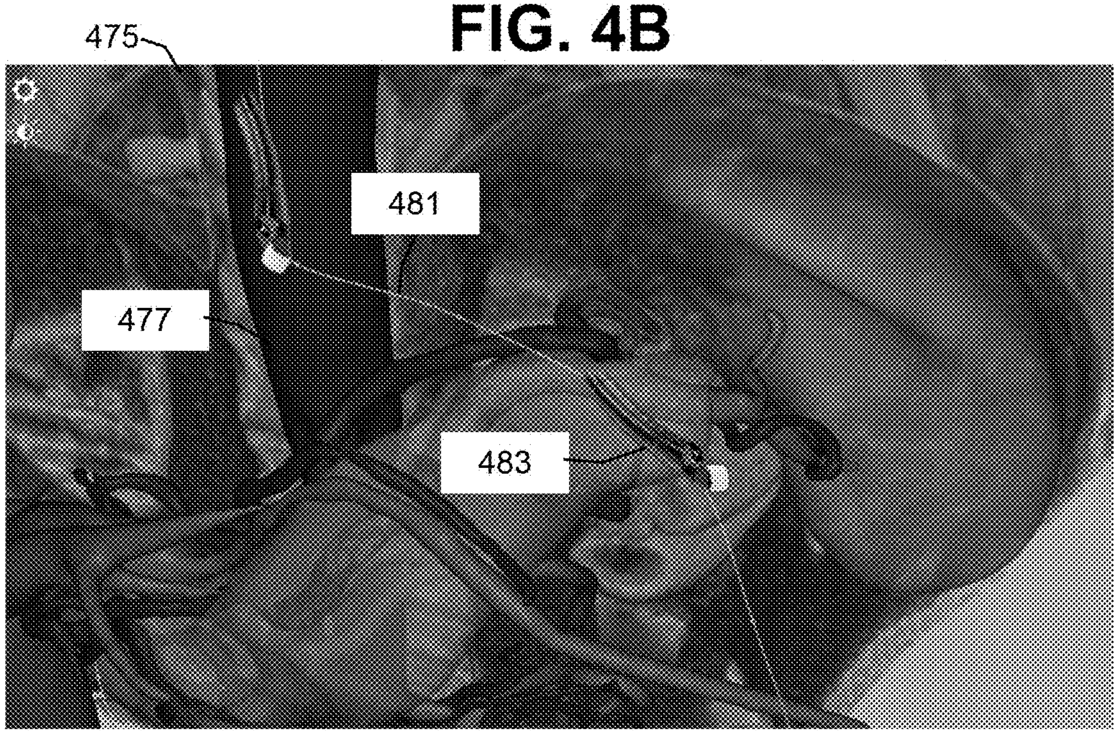

FIGS. 4B and 4C depict different exemplary embodiments of outputs 475 that may be produced by the navigation system 135. As depicted in FIGS. 4B and 4C, an output 475 produced by the navigation system 135 may include one or more of medical imaging data 477 depicting at least a portion of an anatomy of a patient, location information 479 and/or path information 481 overlaid over the medical imaging data 477 and indicating a current and/or past location of the medical device 110, ultrasound imaging data 483 overlaid at corresponding location(s) of the medical imaging data, or the like.

In some embodiments, the navigation system 135, user device 105, touch-screen input of the display 115 or the like is configured to receive an input from a user 140, e.g., to manipulate a perspective of view for the first medical imaging data, to include, move, adjust, and/or remove in the output further information such as the image generated based on the first non-optical in vivo image data or the additional data discussed above.

Returning to FIG. 4A, optionally, at step 445, the medical provider 120 may move the medical device 110, e.g., such that the position of the distal end 205 within the anatomy of the patient changes.

Optionally, at step 450, one or more of steps 415 to step 440 may be iterated, e.g., so as to account for the new position of the distal end 205 of the medical device 110. For example, the navigation system 135 may receive further non-optical in vivo image data from the sensor, and may use the trained machine-learning model to determine an updated location of the distal end 205 of the medical device 110 based on the further non-optical in vivo image data. Further, the navigation system 135 may update the first medical imaging data to adjust the location indicator based on the updated location of the distal end 205 of the medical device 110, and may update the display 115 to output the updated first medical imaging data. In some embodiments, such iteration may occur in real-time or near real-time such that the display 115 is configured to output a live location of the distal end 205 of the medical device 110.

Optionally, at step 455, the navigation may be configured to cause the display 115 to output a target site confirmation upon the navigation system 135 determining that the distal end 205 has reached the target site.

Optionally, at step 460, the medical provider 120 may perform a procedure at the target site using the medical device 110. For example, the medical provider may activate an end effector 230, e.g., an ablation device, in order to ablate tissue at the target site.

Optionally, at step 465, the navigation system 135 and/or the medical provider may confirm completion of the procedure based on further non-optical in vivo image data received from the sensor at the distal end 205. For example, the procedure may involve a modification to the geometry of the anatomy of the patient. The navigation system 135 may be configured to extract one or more modified structures of the anatomy of the patient, and compare the modified structure(s) with previously extracted structure(s). For example, the first medical imaging data may have identified tissue to be ablated, and the navigation system 135 may be configured to identify whether said tissue has been ablated or still persists within the patient.

At step 470, the medical provider 120 may retract the medical device 110 out from the body of the patient. In some embodiments, the medical provider 120 may dispose of the medical device 110.

It should be understood that embodiments in this disclosure are exemplary only, and that other embodiments may include various combinations of features from other embodiments, as well as additional or fewer features. For example, while some of the embodiments above pertain to ablation of tissue within the periphery of the lung. However, any suitable procedure may be used. Further, while some of the embodiments above pertain to ultrasound, any suitable non-optical image modality or technique may be used. In an exemplary embodiment, instead of or in addition to the sensor, the medical device 110 includes a fiber-optic light and a receiver fiber-optic that is usable for position sensing of the distal end 205.

In general, any process or operation discussed in this disclosure that is understood to be computer-implementable, such as the processes illustrated in FIGS. 3 and 4, may be performed by one or more processors of a computer system, such any of the systems or devices in the environment 100 of FIG. 1, as described above. A process or process step performed by one or more processors may also be referred to as an operation. The one or more processors may be configured to perform such processes by having access to instructions (e.g., software or computer-readable code) that, when executed by the one or more processors, cause the one or more processors to perform the processes. The instructions may be stored in a memory of the computer system. A processor may be a central processing unit (CPU), a graphics processing unit (GPU), or any suitable types of processing unit.

A computer system, such as a system or device implementing a process or operation in the examples above, may include one or more computing devices, such as one or more of the systems or devices in FIG. 1. One or more processors of a computer system may be included in a single computing device or distributed among a plurality of computing devices. A memory of the computer system may include the respective memory of each computing device of the plurality of computing devices.

Figure 5:
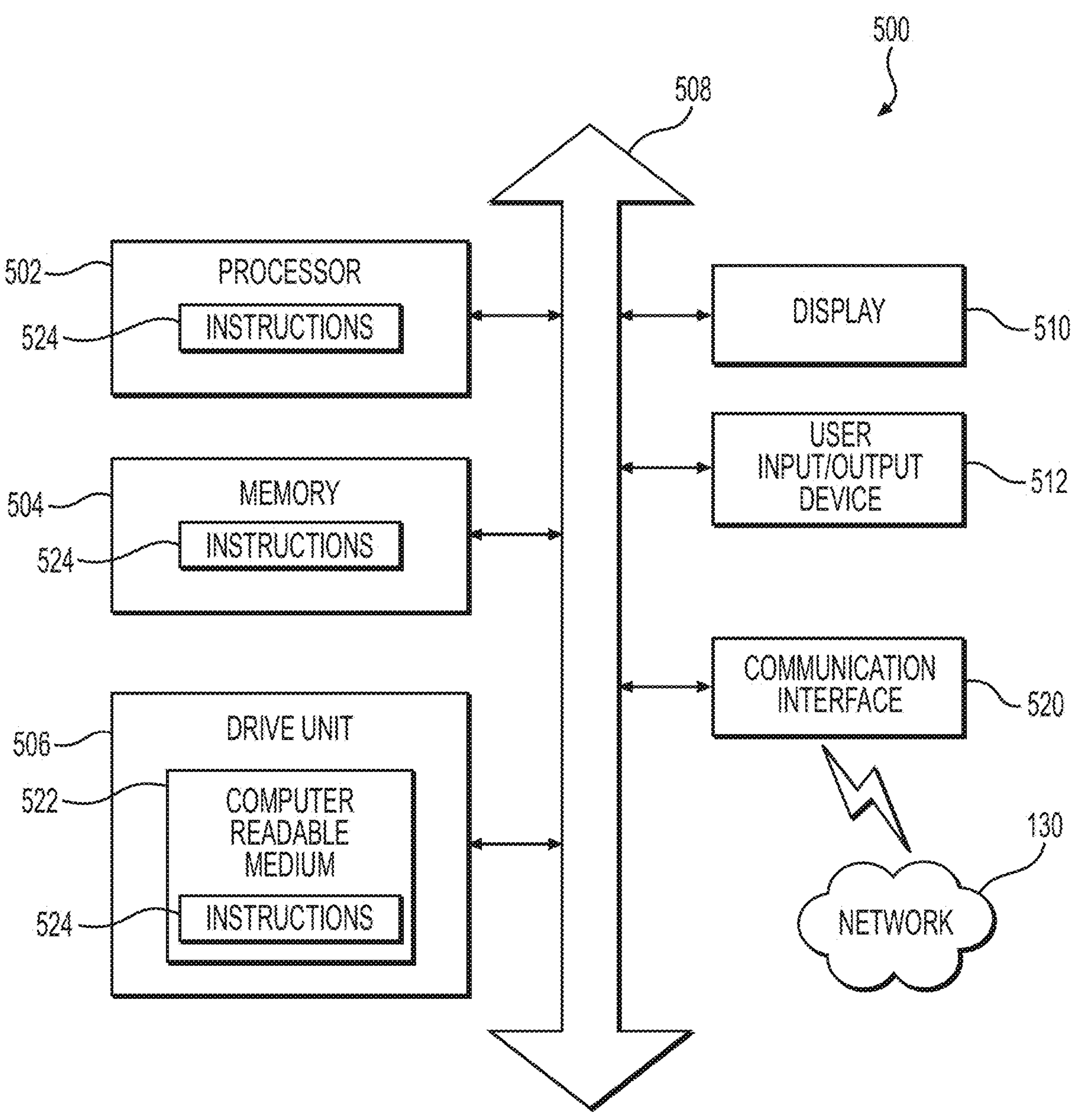
FIG. 5 depicts an example of a computing device, according to one or more embodiments.

FIG. 5 is a simplified functional block diagram of a computer 500 that may be configured as a device for executing the methods of FIGS. 3 and 4, according to exemplary embodiments of the present disclosure. For example, the computer 500 may be configured as the navigation system 135 and/or another system according to exemplary embodiments of this disclosure. In various embodiments, any of the systems herein may be a computer 500 including, for example, a data communication interface 520 for packet data communication. The computer 500 also may include a central processing unit ("CPU") 502, in the form of one or more processors, for executing program instructions. The computer 500 may include an internal communication bus 508, and a storage unit 506 (such as ROM, HDD, SDD, etc.) that may store data on a computer readable medium 522, although the computer 500 may receive programming and data via network communications. The computer 500 may also have a memory 504 (such as RAM) storing instructions 524 for executing techniques presented herein, although the instructions 524 may be stored temporarily or permanently within other modules of computer 500 (e.g., processor 502 and/or computer readable medium 522). The computer 500 also may include input and output ports 512 and/or a display 510 to connect with input and output devices such as keyboards, mice, touchscreens, monitors, displays, etc. The various system functions may be implemented in a distributed fashion on a number of similar platforms, to distribute the processing load. Alternatively, the systems may be implemented by appropriate programming of one computer hardware platform.

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

While the disclosed methods, devices, and systems are described with exemplary reference to transmitting data, it should be appreciated that the disclosed embodiments may be applicable to any environment, such as a desktop or laptop computer, an automobile entertainment system, a home entertainment system, etc. Also, the disclosed embodiments may be applicable to any type of Internet protocol.

It should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Thus, while certain embodiments have been described, those skilled in the art will recognize that other and further modifications may be made thereto without departing from the spirit of the invention, and it is intended to claim all such changes and modifications as falling within the scope of the invention. For example, functionality may be added or deleted from the block diagrams and operations may be interchanged among functional blocks. Steps may be added or deleted to methods described within the scope of the present invention.

The above disclosed subject matter is to be considered illustrative, and not restrictive, and the appended claims are intended to cover all such modifications, enhancements, and other implementations, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. While various implementations of the disclosure have been described, it will be apparent to those of ordinary skill in the art that many more implementations are possible within the scope of the disclosure. Accordingly, the disclosure is not to be restricted except in light of the attached claims and their equivalents.

What is claimed is:

1. A system for providing in vivo navigation of a medical device, comprising:

a memory storing instructions and a trained machine-learning model, wherein:

the trained machine-learning model is trained, based on (i) training medical imaging data and training non-optical in vivo image data of at least a portion of an anatomy of one or more individuals and (ii) registration data associating the training non-optical in vivo image data with locations in the training medical imaging data as ground truth; and the training is configured to cause the trained machine-learning model to learn associations between the training non-optical in vivo image data and the training medical imaging data;

a display; and a processor operatively connected to the display and the memory, and configured to execute the instructions to perform operations, including:

receiving input medical imaging data associated with at least a portion of an anatomy of a patient;

receiving input non-optical in vivo image data from an ultrasound transducer positioned on a distal end of a medical device that is advanced into the portion of the anatomy of the patient;

providing, as input to the trained machine-learning model, the input medical imaging data and the input non-optical in vivo image data, wherein the trained machine-learning model uses the learned associations to determine, and provide as output, a location of the ultrasound transducer, representative of a location of the distal end of the medical device, in the input medical imaging data;

modifying the input medical imaging data to include a location indicator indicative of the determined location of the distal end of the medical device; and causing the display to output the modified input medical imaging data including the location indicator.

2. The system of claim 1, wherein the operations further include:

upon the medical device moving within the portion of the anatomy of the patient, receiving further non-optical in vivo image data from the ultrasound transducer;

providing, as input to the trained machine-learning model, the input medical imaging data and the further non-optical in vivo image data, wherein the trained machine-learning model uses the learned associations to determine an updated location of the ultrasound transducer representative of an updated location of the distal end of the medical device;

updating the input medical imaging data to adjust the location indicator based on the updated location of the distal end of the medical device; and causing the display to output the updated input medical imaging data.

3. The system of claim 2, wherein the determining of the updated location, the updating of the input medical imaging data, and the output via the display of the updated input medical imaging data occur in real-time or near real-time such that the display is configured to output a live location of the distal end of the medical device.

4. The system of claim 1, wherein the trained machine-learning model is configured to learn associations between a sequence of non-optical in vivo images of the training non-optical in vivo image data and a path of travel within the training medical imaging data.

5. The system of claim 4, wherein the trained machine-learning model is configured to determine the location of the distal end of the medical device in the input medical imaging data by predicting a path of travel of the distal end of the medical device from a previous location in the input medical imaging data using the input non-optical in vivo image data.

6. The system of claim 1, wherein:

the operations further include:

extracting at least one three-dimensional structure from the input non-optical in vivo image data; and registering the at least one three-dimensional structure with geometry of the at least portion of the anatomy from the input medical imaging data; and the determination of the location of the distal end of the medical device is further based on the registration of the at least one three-dimensional structure with the geometry.

7. The system of claim 1, wherein the trained machine-learning model includes one or more of a long short term memory network or a sequence-to-sequence model.

8. The system of claim 1, wherein:

the operations further include receiving a position signal from a position sensor positioned proximate to the distal end of the medical device; and the determination of the location of the distal end of the medical device is further based on the position signal.

9. The system of claim 8, wherein:

the operations further include using the position signal to localize a position of the distal end of the medical device to a region within the portion of the anatomy of the patient; and the trained machine-learning model is further configured to use the learned associations to identify the location of the distal end within the localized region.

10. The system of claim 1, wherein the ultrasound transducer includes a phased transducer array, and wherein the input non-optical in vivo image data includes 360 degree image data from the phased transducer array.

11. The system of claim 1, wherein:

the training is configured to associate the training non-optical in vivo image data with diameters of interior portions of anatomy; and using the learned associations, by the trained machine-learning model, to determine the location of the ultrasound transducer, representative of the location of the distal end of the medical device, includes:

using the learned associations to determine a diameter of an interior portion of the anatomy of the patient at a current location of the ultrasound transducer positioned on the distal end of the medical device; and comparing the current diameter with geometry of the input medical imaging data to identify a location in the input medical imaging data matching the determined diameter.

12. The system of claim 1, wherein:

the trained machine-learning model is configured to learn associations between a sequence of diameters determined based on the training non-optical in vivo image data and a path of travel within the training medical imaging data; and the trained machine-learning model is configured to determine the location of the distal end of the medical device in the input medical imaging data by predicting a path of travel of the distal end of the medical device from a previous location in the input medical imaging data using the input non-optical in vivo image data.

13. The system of claim 1, wherein the portion of the anatomy of the patient includes a peripheral portion of a lung of the patient.

14. The system of claim 1, wherein the trained machine-learning model is configured to determine the location of the distal end of the medical device in the input medical imaging data based on shape information associated with the medical device received from a further sensor of the medical device.

15. The system of claim 1, wherein the non-optical in vivo image data from the ultrasound transducer is the only sensor data provided as input to the trained machine-learning model for use in determining the location of the ultrasound transducer, representative of the location of the distal end of the medical device, in the input medical imaging data.

16. A method for providing in vivo navigation of a medical device, comprising:

receiving input medical imaging data associated with at least a portion of an anatomy of a patient;

receiving input non-optical in vivo image data from a sensor positioned on a distal end of a medical device that is advanced into the portion of the anatomy of the patient;

extracting at least one three-dimensional structure from the input non-optical in vivo image data;

registering the at least one three-dimensional structure with geometry of the at least portion of the anatomy from the input medical imaging data;

using a trained machine-learning model to determine a location of the distal end of the medical device in the input medical imaging data based on the input medical imaging data, the input non-optical in vivo image data, and the registration of the at least one three-dimensional structure with the geometry, wherein:

the trained machine-learning model is trained, based on (i) training medical imaging data and training non-optical in vivo image data of at least a portion of an anatomy of one or more individuals and (ii) registration data associating the training non-optical in vivo image data with locations in the training medical imaging data as ground truth;

the training is configured to cause the trained machine-learning model to learn associations between the training non-optical in vivo image data and the training medical imaging data, and the trained machine-learning model is configured to use the learned associations to determine the location of the distal end of the medical device in the input medical imaging data;

modifying the input medical imaging data to include a location indicator indicative of the determined location of the distal end of the medical device; and causing a display to output the modified input medical imaging data including the location indicator.

17. The method of claim 16, wherein:

the input non-optical in vivo image data is ultrasound data; and the portion of the anatomy of the patient includes a peripheral portion of a lung of the patient.

18. A method of training a machine-learning model to determine an output location of a distal end of a medical device in an anatomy of a patient within input medical imaging data in response to receiving the input medical imaging data and receiving, from a sensor positioned on the distal end of a medical device, input non-optical in vivo image data, the method comprising:

inputting training data into the machine-learning model, the training data including training medical imaging data and training non-optical in vivo image data of at least a portion of an anatomy of one or more individuals;

inputting ground truth into the machine-learning model that includes registration data associating the training non-optical in vivo image data with locations in the training medical imaging data, the registration data generated by extracting at least one three-dimensional structure from the training non-optical in vivo image data, and registering the at least one three-dimensional structure with geometry of the at least portion of the anatomy from the training medical imaging data; and using the training data and the ground truth with the machine-learning model to learn associations between the training non-optical in vivo image data and the training medical imaging data that are usable by the machine-learning model to determine the output location of the distal end of the medical device.

19. The method of claim 18, further comprising:

using the training data and the ground truth with the machine-learning model to learn associations between a sequence of training non-optical in vivo images and a path of travel within the training medical imaging data, such that the the machine-learning model is configured to determine the location of the distal end of the medical device in the input medical imaging data by predicting a path of travel of the distal end of the medical device from a previous location in the input medical imaging data using the input non-optical in vivo image data.

20. The method of claim 18, wherein the training non-optical in vivo image data is ultrasound data.

* * * * *